(12) United States Patent
Momose et al.

(10) Patent No.: US 9,715,728 B2
(45) Date of Patent: Jul. 25, 2017

(54) BRAIN TOMOGRAPHIC DYNAMIC IMAGE ANALYZING APPARATUS

(71) Applicants: SHIMADZU CORPORATION, Kyoto (JP); The University of Tokyo, Tokyo (JP); FUJIFILM RI PHARMA CO., LTD., Tokyo (JP)

(72) Inventors: Toshimitsu Momose, Tokyo (JP); Tomohiko Sato, Kyoto (JP); Tsutomu Soma, Tokyo (JP); Daisuke Saito, Tokyo (JP); Miwako Takahashi, Tokyo (JP); Keisuke Ogaki, Tokyo (JP)

(73) Assignees: SHIMADZU CORPORATION, Kyoto (JP); THE UNIVERSITY OF TOKYO, Tokyo (JP); FUJIFILM RI PHARMA CO., LTD., Tokyo (JP)

( * ) Notice: Subject to any disclaimer, the term of this patent is extended or adjusted under 35 U.S.C. 154(b) by 7 days.

(21) Appl. No.: 14/424,870

(22) PCT Filed: Aug. 28, 2013

(86) PCT No.: PCT/JP2013/073007
§ 371 (c)(1),
(2) Date: Feb. 27, 2015

(87) PCT Pub. No.: WO2014/034724
PCT Pub. Date: Mar. 6, 2014

(65) Prior Publication Data
US 2015/0235358 A1  Aug. 20, 2015

(30) Foreign Application Priority Data
Aug. 30, 2012  (JP) .................................. 2012-190107

(51) Int. Cl.
*G06K 9/00* (2006.01)
*G06T 7/00* (2017.01)
(Continued)

(52) U.S. Cl.
CPC .............. *G06T 7/0012* (2013.01); *G06K 9/46* (2013.01); *G06K 9/52* (2013.01); *G06K 9/6202* (2013.01);
(Continued)

(58) Field of Classification Search
None
See application file for complete search history.

(56) References Cited

U.S. PATENT DOCUMENTS

| 8,094,894 B2 * | 1/2012 | Nagler | ..................... A61B 6/00 382/128 |
| 2008/0033291 A1 * | 2/2008 | Rousso | .............. A61B 5/02755 600/436 |

(Continued)

FOREIGN PATENT DOCUMENTS

| JP | 2003-199715 A | 7/2003 |
| WO | 2010/032472 A1 | 3/2010 |

OTHER PUBLICATIONS

English translation International Search Report PCT/JP2013/073007 dated Oct. 29, 2013.
(Continued)

*Primary Examiner* — Hadi Akhavannik
(74) *Attorney, Agent, or Firm* — McDermott Will & Emery LLP (57) ABSTRACT

In order to provide a tomographic image analyzing apparatus which is simple and which obtains stable results, the tomographic image analyzing apparatus according to this invention includes an image standardizing unit which transforms PET images, in advance of tomographic image analysis, so that the contour of the brain of an subject appearing in the PET images become the contour of a brain represented by standard data. By carrying out such transforming operation before the analysis, there is no need to acquire MRI images like before, to be able to ease the burden on the
(Continued)

subject. And according to this invention, the time of analysis is shortened. Further, according to this invention, an analysis of time variations of radioactive drug distribution is conducted with respect to a corresponding site on standardized PET images which corresponds to the ROI on the standard data. This can make analysis results stable.

8 Claims, 4 Drawing Sheets (51) Int. Cl.
      *G06K 9/52*       (2006.01)
      *G06K 9/46*       (2006.01)
      *G06K 9/62*       (2006.01)

(52) U.S. Cl.
      CPC ............... *G06K 2009/4666* (2013.01); *G06T 2207/30016* (2013.01)

(56) References Cited

U.S. PATENT DOCUMENTS

2009/0252391 A1* 10/2009 Matsuda ............... A61B 5/055
                                                                               382/131
2011/0172522 A1     7/2011 Shuki

OTHER PUBLICATIONS

Notification of Reasons for Refusal Japanese Patent Application No. 2014-533047 dated Dec. 8, 2015 with English translation.

* cited by examiner

DISTRIBUTION IMAGE
STANDARDIZING
PROCESS

IMAGE ANALIZING
PROCESS

BRAIN TOMOGRAPHIC DYNAMIC IMAGE ANALYZING APPARATUS

RELATED APPLICATIONS

This application is the U.S. National Phase under 35 U.S.C. §371, of International Application No. PCT/JP2013/073007, filed on Aug. 28 2013, (which in turn claims the benefit of Japanese Application No. 2012-190107, filed on Aug. 30 2013), the disclosures of which Applications are incorporated by reference herein.

TECHNICAL FIELD

This invention relates to a tomographic image analyzing apparatus for analyzing tomographic images picked up continuously with respect to a time axis, and more particularly to a tomographic image analyzing apparatus for analyzing tomographic images especially with respect to functional images.

BACKGROUND ART

A medical institution has a radiation tomographic imaging apparatus for imaging tomographic images of subjects with radiation. As such a radiation tomographic imaging apparatus, there is a PET (Positron Emission Tomography) apparatus which images a radioactive drug in an subject, for example.

Tomographic images with the PET apparatus are images when the subject is cut at certain planes, in which densities of the radioactive drug are represented by luminance. How the radioactive drug moves within the subject can be grasped by generating dynamic tomographic images picked up continuously in one inspection within a fixed period of time. Or the metabolism and accumulation in the subject of the radioactive drug can be known from static tomographic images obtained by one shooting after lapse of a fixed period of time.

The PET apparatus is used for diagnosis relating to the brain such as Alzheimer's disease. In such diagnosis, the subject is administered and injected with a drug labeled with radioisotope and binding to brain amyloid protein, and diagnosis is carried out to check the behavior within the brain of this drug.

In order to conduct a diagnosis using such tomographic images, dynamic tomographic images of the brain of the subject are acquired first. Then, an analysis is carried out on time variations within a fixed period of time of radioactive drug density in a specific site within the brain shown in the tomographic images. Such analysis enables a diagnosis based on functional images of the specific site. The functional images are a generic name for images showing various activities of the brain, which are distinguished from form images showing structures such as sulci and hollows of the brain. The tomographic images acquired at this time will be called herein dynamic PET images.

Incidentally, in conducting diagnoses with functional images, one site of tomographic images is often designated as a region of interest (ROI). An analysis is conducted using this designated ROI as a specific site. The ROI designated at this time is cerebellar cortex, for example. Since there are individual differences in the shape of brain, the shape of the cerebellar cortex is also different between individuals. Therefore, the ROI needs to be designated individually by recognizing the shape of cerebellar cortex of an individual.

So, according to a conventional construction, when designating a site of interest, reference is made to static PET images or form images enabling recognition of the ROI. The form images are static tomographic images in which the internal shape of the brain is imaged. These form images are acquired with an MRI apparatus or CT apparatus before or after imaging by the PET apparatus. The dynamic tomographic images acquired with the PET apparatus represent a distribution of densities of a radioactive drug, and not images showing the internal shape of the brain, which cannot be used for designating of the ROI.

That is, in conducting an image analysis using the PET apparatus, the conventional construction uses static PET images or form images enabling grasp of the internal shape of the brain. In that case, for setting the ROI, there are a method which sets it to the shape of the brain of an subject, and a method which converts the shape of the brain of an subject into a standard brain shape determined beforehand, and sets thereon a standard ROI determined beforehand (see Patent Document 1, for example).

PRIOR ART DOCUMENT

Patent Document

[Patent Document 1] Unexamined Patent Publication No. 2003-199715

SUMMARY OF INVENTION

Technical Problem

However, the conventional image analysis has the following problems.

That is, for the conventional image analysis, static PET imaging or image pickup for form images must be carried out in addition to dynamic PET imaging. According to the conventional method, the analysis of the dynamic PET images requires static PET imaging or radiography for form images. That is, the diagnosis takes all the longer time for this reason.

When the ROI is manually designated in the conventional method, variations will occur to the ROI designated. That is, variations will occur in the way the cerebellar cortex appears in the static PET tomographic images or the form images, and in shape and size of the ROI due to the operator's peculiarity. Or when there are neither static PET tomographic images nor form images, the site of interest must be estimated from dynamic PET images. Then, variations will occur also to results of the analysis. The situation where the image analysis is dependent on the operator's subjectivity in this way is not desirable from the viewpoint of obtaining stable results.

This invention has been made having regard to the state of the art noted above, and its object is to provide a tomographic image analyzing apparatus which obtains accurate and stable results from dynamic PET images by a simple operation.

Solution to Problem

To fulfill the above object, this invention provides the following construction.

A tomographic image analyzing apparatus according to this invention is a tomographic image analyzing apparatus for analyzing dynamic distribution images which are tomographic images showing distributions of a radioactive drug, the apparatus comprising a storage device storing beforehand standard data showing a shape of a standard brain; a distribution image standardizing device generating a standardized distribution image having a distribution of the radioactive drug standardized for each of the dynamic distribution images, by transforming each of the dynamic distribution images so that a form of a brain of an subject appearing in the dynamic distribution images become a form of the brain shown by the standard data; and an analyzing device carrying out an analysis of time variations of radioactive drug distribution based on the standard data.

An analysis program according to this invention is an analysis program for causing a computer to execute an analysis of dynamic distribution images which are tomographic images showing distributions of a radioactive drug, the program causing the computer to function as a standard data readout device reading standard data stored beforehand in the computer and showing a standard shape; a distribution image standardizing device generating a standardized distribution image having a distribution of the radioactive drug standardized for each of the dynamic distribution images, by transforming each of the dynamic distribution images so that a form of a brain of an inspection object appearing in the dynamic distribution images become a form of the brain shown by the standard data; and an analyzing device carrying out an analysis of time variations of radioactive drug distribution based on the standard data.

[Functions and effects] The tomographic image analyzing apparatus according to this invention includes the distribution image standardizing device which transforms the dynamic distribution images, in advance of a tomographic image analysis, so that the form of the brain of the subject appearing in the distribution images become the form of the brain shown by the standard data. According to this invention, therefore, it is not necessary to acquire static PET images or form images besides dynamic PET images corresponding to the dynamic distribution images about the brain of the subject appearing in the distribution images. Consequently, compared with conventional techniques, this invention can ease the burden on the subject. Further, the time of analysis is shortened since it is not necessary to carry out varied image processes which refer to these static PET images or form images.

And according to this invention, the standardized distribution image is generated for each of the dynamic distribution images by transforming the dynamic distribution images which have no form information or which cannot be standardized alone. It is constructed to be able to acquire, as values, temporal density variations in a ROI obtained from form images based on the dynamic distribution images.

This invention may be realized in the form of an analysis program for causing a computer to execute equivalent operations, and a storage medium which stores same.

In the tomographic image analyzing apparatus noted above, it is preferable to comprise a transform function acquiring device acquiring a transform function for use by the distribution image standardizing device when transforming the dynamic distribution images, by comparing a distribution form display image selected from the dynamic distribution images of the subject and enabling recognition of the form of the brain, and the form of the brain shown by the standard data.

[Functions and effects] The above construction shows a more specific construction of this invention. That is, the transform function used by the dynamic distribution image standardizing device when transforming the dynamic distribution images is acquired by the transform function acquiring device. With such construction, the tomographic image analyzing apparatus of this invention operates reliably.

In the tomographic image analyzing apparatus noted above, it is preferable to comprise a storage device storing beforehand a ROI on the standard data; wherein the analyzing device carries out an analysis of time variations of the radioactive drug distribution about a corresponding site on the standardized distribution images which corresponds to the ROI on the standard data.

[Functions and effects] According to the above construction, the following analysis is conducted concerning the standardized distribution images generated after transformation. That is, an analysis of time variations of radioactive drug distribution in the corresponding site on the standardized distribution images which corresponds to the ROI on the standard data is conducted using, as they are, numerical values indicating time variations of the radioactive drug distribution. Such measure assures highly accurate and stable analysis results. According to a conventional technique, form images are made available, and a ROI is manually set to dynamic distribution images for each subject. Alternatively, these form images are used for transformation into standard data, and a ROI is set. This invention, however, can automatically carry out this setting of a ROI without making available form images other than the dynamic distribution images. This realizes shortening of the analysis time, and eliminates room for entry of subjectivity to render results of the analysis stable.

In the tomographic image analyzing apparatus noted above, it is preferable to comprise a normalizing device normalizing analysis results of the analyzing device based on analysis results in the corresponding site on the standardized distribution images.

[Functions and effects] The above construction shows a more specific construction of this invention. The construction for normalization as in this invention can conduct image analysis with increased flexibility and diversity.

In the tomographic image analyzing apparatus noted above, it is preferable that the storage device stores a pattern of the time variations of the radioactive drug; and a comparing device is provided for comparing the analysis results of the analyzing device and the pattern.

In the tomographic image analyzing apparatus noted above, it is preferable that the storage device stores analysis results of a normal brain outputted by the analysis device; and the comparing device compares the analysis results of the analyzing device and the analysis results of the normal brain.

In the tomographic image analyzing apparatus noted above, it is preferable that the storage device stores past analysis results outputted by the analyzing device; and the comparing device compares the analysis results of the analyzing device and the past analysis results.

[Functions and effects] The above construction represents an example of analysis of tomographic images. The construction of this invention is applicable to various analyzing methods. In particular, according to this invention, since there is little necessity for using manual operation at the time of analysis, it becomes easy to acquire analysis results automatically.

In the tomographic image analyzing apparatus noted above, it is preferable to comprise a ROI individualizing device transforming a ROI on the standard data by a transformation mode which changes the shape of the brain shown by the standard data into the shape of the brain of the subject appearing in the dynamic distribution images, and acquiring a ROI on the distribution images.

[Functions and effects] According to the above construction, a ROI individualizing device is provided for acquiring a ROI on the distribution images by transforming a ROI on the standard data. Such construction enables a grasp of information on varied sites of interest within the brain of the inspection object easily and conveniently.

Advantageous Effects of Invention

The tomographic image analyzing apparatus according to this invention includes the distribution image standardizing device which transforms the dynamic distribution images, in advance of a tomographic image analysis, so that the form of the brain of the subject appearing in the distribution images become the form of the brain shown by the standard data. By carrying out such transforming operation before the analysis, there is no need to acquire static PET images or form images separately like before, to be able to ease the burden on the subject. Further, this invention shortens the time of analysis. Further, according to this invention, an analysis of time variations of the dynamic distribution images is conducted by automatically acquiring numerical values of radioactive drug distribution with respect to a corresponding site on dynamic standardized distribution images which corresponds to the ROI on the standard data. This can make analysis results highly accurate and stable.

DESCRIPTION OF EMBODIMENTS

Embodiments of this invention will be described hereinafter.

Embodiment 1

<Outline of Processes Carried Out by the Tomographic Image Analyzing Apparatus>

Figure 1:
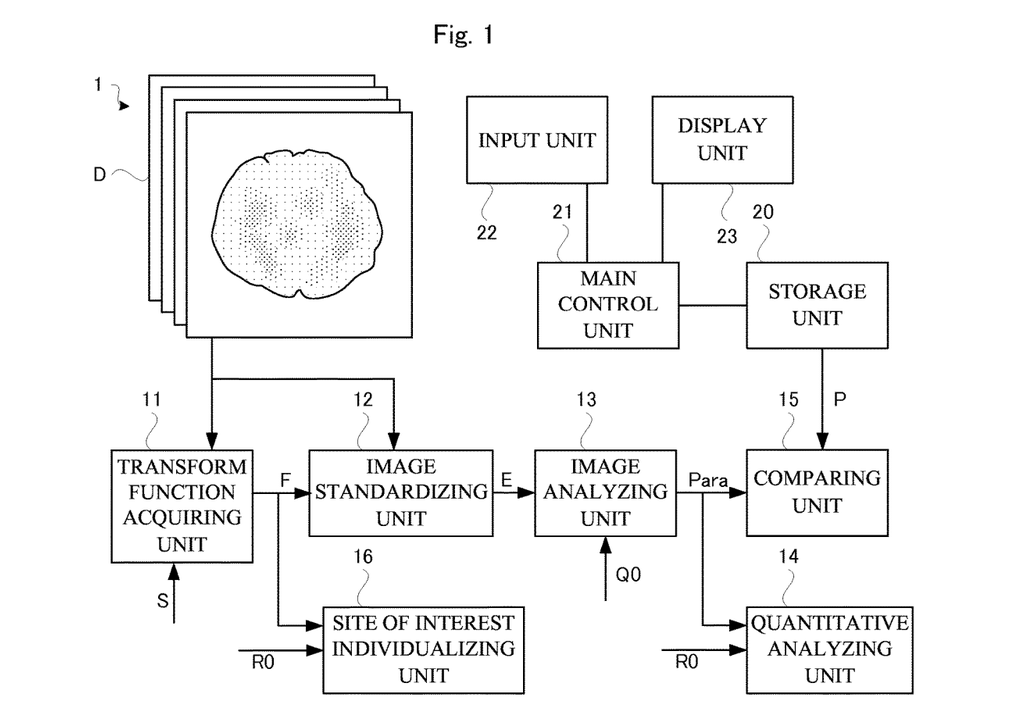
FIG. 1 is a functional block diagram illustrating an overall construction of a tomographic image analyzing apparatus according to this invention.

A tomographic image analyzing apparatus 1 according to Embodiment 1, as shown in FIG. 1, when PET images D imaged with a PET apparatus are inputted, carries out various image processes, and whether a distribution situation of a radioactive drug taken into the PET images D acquired dynamically is abnormal is determined by an image analyzing unit 13. That is, the tomographic image analyzing apparatus 1 of this invention is intended to analyze the PET images D which are tomographic images showing distributions of the radioactive drug.

The PET images D are tomographic images obtained by administering, through injection, an subject with a compound (radioactive drug) labeled by a positron emission type nuclide which produces annihilation gamma-ray pairs, and tracing the radioactive drug. More particularly, they are tomographic images which show a distribution situation within the brain of the radioactive drug obtained by detecting pairs of gamma rays generated from the radioactive drug. The PET images D therefore show densities of the radioactive drug within the brain in color-coding.

Thus, the PET images D represent density distributions of the radioactive drug on a slice plane crossing the brain. In imaging with the PET apparatus, radiography of these PET images D is carried out a plurality of times sequentially. The tomographic image analyzing apparatus 1 therefore receives a plurality of PET images D acquired at different shooting times though of the same slice plane. When looking at these PET images D in the order of time series, it can be seen how the distribution of the radioactive drug changes in the brain. Such a change in the distribution of the radioactive drug shows whether an abnormality is present in the brain of the subject. However, even if the PET images D are simply placed in order and studied, it is difficult to diagnose accurately whether the brain is normal. Therefore, an analysis by the tomographic image analyzing apparatus 1 as in this invention is needed for diagnosis based on the PET images D.

Incidentally, since the PET images D show a distribution situation of the radioactive drug within the brain, it may seem naturally that the form of the brain of the subject is depicted therein. However, it is not necessarily so in practice. Only a small portion of the brain appears in the PET images D acquired by imaged immediately after administration of the radioactive drug. This is because such PET images D are imaged in a state where the radioactive drug administered by injection and borne by the blood flow has not fully circulated in the brain. Part of the brain may not appear also in PET images acquired just before the end of a continuous shooting of the PET images D. This is because the radioactive drug may be accumulated in a particular site within the brain through the blood flow. FIG. 1 shows those of the PET images D acquired dynamically that depict the cerebral form. The same applies to the other figures.

<Overall Construction of the Tomographic Image Analyzing Apparatus>

An overall construction of the tomographic image analyzing apparatus 1 will be described. The tomographic image analyzing apparatus 1 includes an image standardizing unit 12 for transforming the PET images D into agreement with standard data, and a transform function acquiring unit 11 for acquiring a transform function F for use when the image standardizing unit 12 transforms the PET images D. Further, the tomographic image analyzing apparatus 1 includes the image analyzing unit 13 and a quantitative analyzing unit 14 for analyzing time variations of the radioactive drug distribution in standardized PET images D. A comparing unit 15 is constructed for comparing results of the analysis by the image analyzing unit 13, and results of an analysis outputted in the past from the image analyzing unit 13 or results of an analysis outputted beforehand from the image analyzing unit 13 about a normal subject. A ROI individualizing unit 16 is constructed for acquiring the position, range and size of a ROI of the brain measured, and a specific construction thereof will be described hereinafter.

The main control unit 21 is provided for the purpose of performing overall control of the components. This main control unit 21 is formed of a CPU, and realizes each of the units 11, 12, 13, 14 and 15 by executing varied programs. A storage unit 20 stores all images and parameters required for the analysis, such as standard data S showing the shape of a standard brain, data showing sites of interest Q0, R0 on the standard data S, a pattern P of time variations of the radioactive drug, and the results of the analysis outputted in the past from the image analyzing unit 13. In addition, the tomographic image analyzing apparatus 1 includes an input unit 22 for the operator to input instructions, and a display unit 23 for outputting and displaying results of analyses. The main control unit 21 corresponds to the computer in this invention.

<About the Standard Data>

Figure 2:
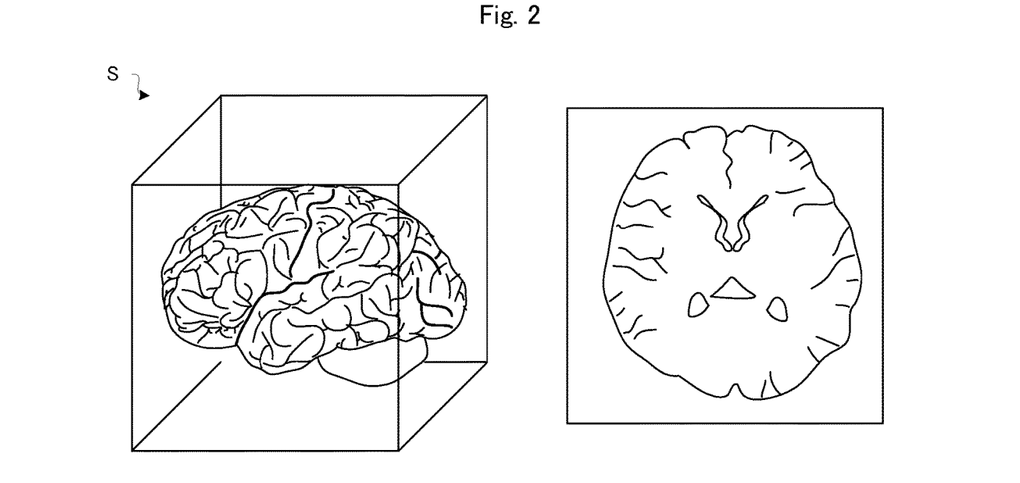
FIG. 2 is a schematic view illustrating standard data according to this invention.

FIG. 2 is a conceptual representation of the standard data S stored in the storage unit 20 showing the shape of a standard brain in data form. The standard data S is 3D image data representing the shape of a standard brain in three dimensions as shown in the left portion of FIG. 2. The standard brain is a form of the brain serving as reference for identifying sites within the brain. And this standard data S is data also showing the interior construction of the standard brain. Therefore, when a two-dimensional image is created as if by cutting the standard brain at a certain slice plane, an interior construction of the brain will appear as shown in the right portion of FIG. 2. This standard brain has already been analyzed to determine which position corresponds to which structure. Thus, all analyses have been done to determine which part of the range constituting the standard data S corresponds to the hippocampus, and which part corresponds to the cerebellar cortex.

The sites of interest Q0, R0 on the standard data S are part areas of the standard data S, which represent the positions, ranges and sizes of structures within the standard brain. The sites of interest Q0, R0 can be freely selected according to a purpose of diagnosis. For example, the sites of interest Q0, R0 may be set to the hippocampus, or may be set to the cerebellar cortex.

The pattern P of time variations of the radioactive drug are stored in the storage unit 20 as a tomographic image showing the pattern P of time variations of the radioactive drug in the normal brain, which is one tomographic image numerically expressing a state of intracerebral behavior of the radioactive drug. The storage unit 20 additionally stores an image representing a pattern P of time variations of the radioactive drug in an abnormal brain. These patterns P are obtained by arranging, in the interior of the standard brain, pixels representing an intracerebral behavior situation of the radioactive drug. The patterns P are therefore parametric images of the standard brain. The parametric images in this case are, in simple terms, functional images showing temporal analysis results of the PET images D acquired dynamically.

Incidentally, such patterns P are acquired by measuring the brain with a PET apparatus. However, the problem here is that dynamic distribution images of the measured brain do not show the shape of the standard brain. So, in order to generate patterns P, according to a conventional method, the shape of the brain used is radiographed with a tomographic apparatus for form images, such as static PET imaging, MRI apparatus or CT apparatus, before or after measurement for dynamic PET image pickup. Since the shape of the brain measured can be seen from static PET images or form images which must enable recognition of the position, range and size of a structure within the brain, it is possible to acquire a transformation mode for turning the shape of the measured brain into the shape of the standard brain. Therefore, by transforming the tomographic images obtained with the PET apparatus by the same transformation mode, the brain appearing in the tomographic images is transformed into the shape of the standard brain. By operating the image standardizing unit 12 described hereinafter, the patterns P can be acquired without conducting static PET imaging or form image radiography.

<Operation of the Tomographic Image Analyzing Apparatus>

Next, operation of the tomographic image analyzing apparatus will be described. The most salient characteristic of this invention lies in that a tomographic image analysis is completed by a dynamic PET image pickup alone without separately performing static PET imaging or form image radiography for specifying a ROI before or after the PET imaging. This construction will be described in detail. First, the PET images D obtained with a PET apparatus are sent to the transform function acquiring unit 11. The transform function acquiring unit 11 acquires a transform function F which transforms the shape of the brain of the subject appearing in the PET images D into the shape of the standard data based on the PET images D and standard data S.

<Operation of the Transforming Function Acquiring Unit>

Figure 3:
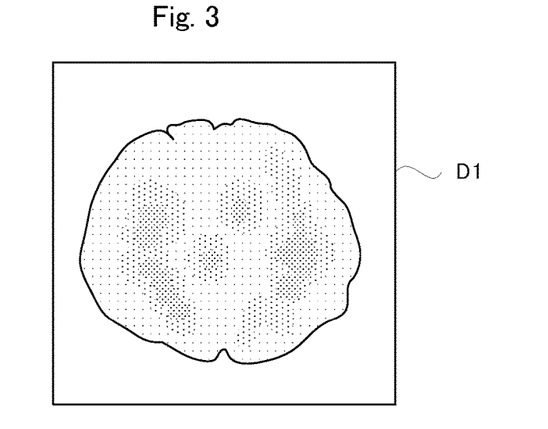
FIG. 3 is a schematic view illustrating a form display image of dynamic distribution images according to this invention.

The transform function acquiring unit 11 selects an appropriate image set showing the form of the brain from among the plurality of PET images D of the same slice plane obtained by dynamic PET imaging, and calculates an additive average thereof to generate a distribution form display image D1 showing the shape of the brain measured with the PET apparatus. This distribution form display image D1, as shown in FIG. 3, is an image clearly showing the shape of the brain. What serves as an index when the transform function acquiring unit 11 selects PET images D is, for example, time taken from injection of the radioactive drug to imaging. It is known that, after injection of the radioactive drug, the radioactive drug will pervade the entire brain in a certain period of time. The transform function acquiring unit 11 generates the distribution form display image D1 by totaling the PET images imaged before or after this period of time. This distribution form display image D1 represents the form of the brain measured with the PET apparatus.

Figure 4:
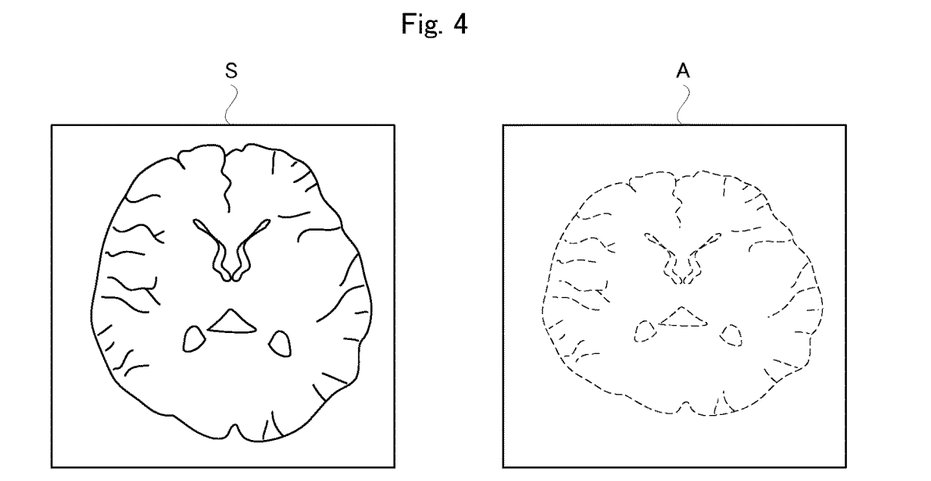
FIG. 4 is a schematic view illustrating a principle of acquisition of a transform function according to this invention.

The transform function acquiring unit 11 acquires the transform function using this distribution form display image D1, and a principle thereof will be described. The left portion of FIG. 4 shows the standard data S depicting the standard brain. Here, the standard data S is depicted as a tomographic image for expediency of description. And the right portion of FIG. 4 is a hypothetical image A showing a structural image of a brain measured with a PET apparatus. This hypothetical image A is obtained by conventional static PET imaging or form image imaging. However, this is not an image actually obtained since static PET imaging or form image imaging is not carried out in this invention. In view of such a situation, FIG. 4 depicts the hypothetical image A in broken lines.

Figure 5:
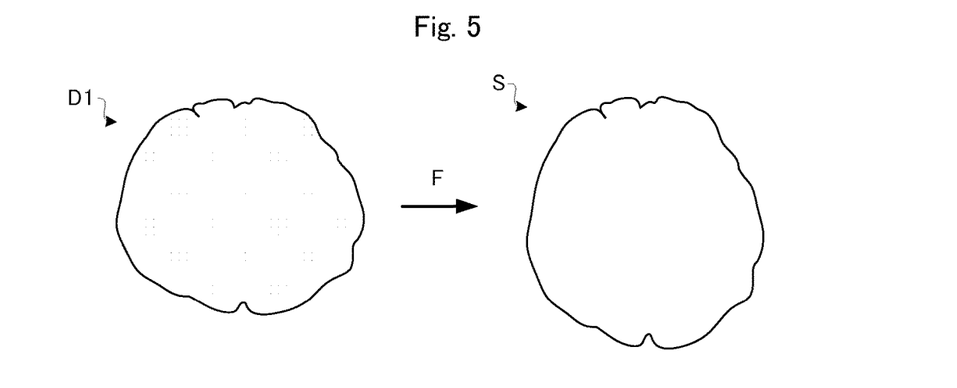
FIG. 5 is a schematic view illustrating the principle of acquisition of the transform function according to this invention.
Figure 6:
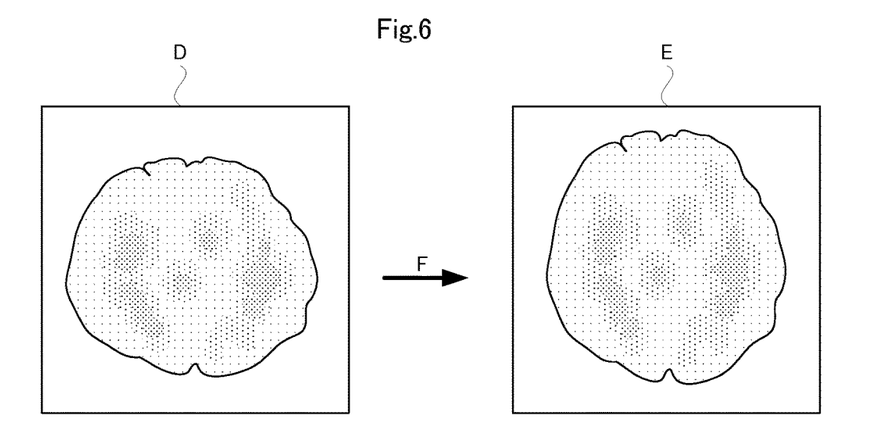
FIG. 6 is a schematic view illustrating operation of an image standardizing unit according to this invention.

It is true that the hypothetical image A cannot be obtained by imaging with a PET apparatus. However, the form of a brain can be acquired even with a PET apparatus. The distribution form display image D1 represents the form of a brain measured with this very PET apparatus. That is to say, a transform function F is conceivable which, as shown in FIG. 5, transforms the form of the brain appearing in the distribution form display image D1 into the form of the brain indicated by the standard data S. The transform function acquiring unit 11 acquires a transform function F which transforms the form of the brain of the subject appearing in the distribution form display image D1 into the form of the brain indicated by the standard data S, by comparing the form of the brain of the subject appearing in the distribution form display image D1 resulting from those enabling recognition of the form of the brain selected from the PET images D acquired dynamically, and the form of the brain indicated by the standard data S. When this transform function F is applied to the distribution form display image D1, the brain appearing in the image transforms into the shape of the standard brain as shown in FIG. 6. That is, the transform function F is a function that can standardize the form of the brain.

<Significance of the Transform Function>

Assume, for example, that a section of the hippocampus is included in the PET images D. Although the hippocampus is located somewhere inside the PET images D, a look at the PET images D cannot determine which portion is the hippocampus. This is because the PET images D represent no more than distributions of the radioactive drug. Now, when the transform function F is applied the PET images D, the form of the entire brain on the PET images D are transformed into the form of the standard brain, and in accordance therewith the portions of the hippocampus on the PET images D are similarly transformed. However, it is difficult to guess the position of the hippocampus on the images only by looking at standardized PET images E generated by applying the transform function F to the PET images D (see FIG. 6).

However, the position of the hippocampus in the standard brain is known beforehand. This is because the standard brain is generated from other form images such as MRI images showing the internal structure of the brain. On the other hand, a brain in the form of the standard brain appears in the standardized PET images E. These standardized PET images E are, so to speak, PET images when the brain radiographed with the PET apparatus is assumed to have the shape of the standard brain. That is to say, none other than the hippocampus is located in the areas on the standardized PET images E which are in the same positions as the positions where the hippocampus lies in the standard brain. By determining beforehand in this way the position of the structure such as the hippocampus on the standard brain, it is possible to know the position of the hippocampus with respect to the brain measured with the PET apparatus.

<Operation of the Image Standardizing Unit>

The transform function F is sent to the image standardizing unit 12. The image standardizing unit 12 generates a standardized PET image E for each of the PET images D by applying the transform function F to each of the dynamic PET images D. This transforms the PET images D so that the form of the brain of the subject appearing in each of the PET images D become the form of the brain indicated by the standard data S, thereby to standardize the distributions of the radioactive drug. If the standardized PET images E are seen in the order of imaging of the corresponding PET images D, it is possible to know a transition of the distributions of the radioactive drug when the brain used in the imaging with the PET apparatus temporarily becomes the shape of the standard brain. Incidentally, certain of the PET images D acquired dynamically show an entire image of the brain, and the others do not. That is to say, the image standardizing unit 12 will effect transformation of the PET images D imaging at different times, including the PET images D showing the form of the brain of the subject, and the PET images D not showing the form of the brain of the subject.

<Operation of the Image Analyzing Unit>

Figure 7:
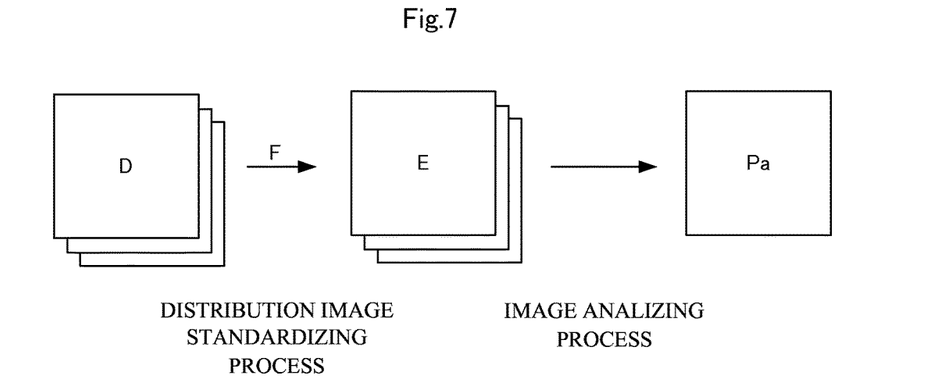
FIG. 7 is a schematic view illustrating an outline of image processing according to this invention.

The plurality of standardized PET images E are sent to the image analyzing unit 13. The image analyzing unit 13 conducts an image analysis of the standardized PET images E by generating a parametric image Pa showing density variations of the radioactive drug in the entire brain. That is, the image analyzing unit 13 generates a parametric image Pa as shown in FIG. 7. This parametric image Pa is generated, for example, by conducting the following analysis of every pixel forming the standardized PET images E. First, of the pixels forming the standardized PET images E corresponding to the dynamic PET images D, pixel values are acquired for every point of time of imaging from target sites showing different behaviors from reference sites showing the same behavior regardless of normal or diseased, and these are plotted on a graph as related to the points of time of imaging by a mathematical technique of time integration. Whether the target sites are healthy sites or diseased sites can be known by checking inclinations occurring when this plot is put to a first-order approximation.

An inclination of a first-order approximation straight line is generated for each of all the pixels forming the PET images, instead of the ROI R0, leaving the data of the ROI R0 intact. By arranging such inclinations corresponding to positions of the pixels, the parametric image Pa can be generated to show the standard brain (more accurately, the brain measured and standardized) as color-coded according to the degrees of the straight line inclinations. Therefore, only one parametric image Pa is acquired for one slice plane.

Figure 8:
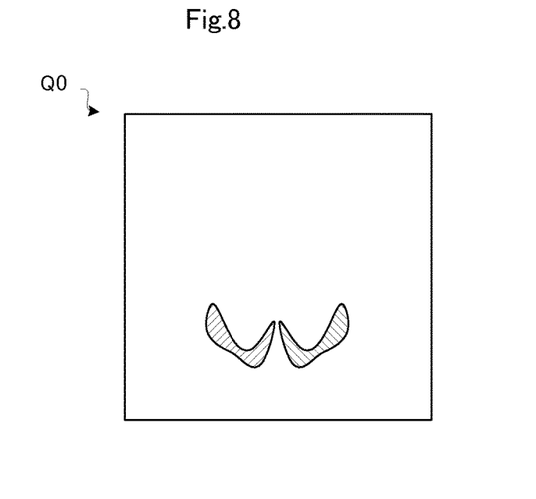
FIG. 8 is a schematic view illustrating a ROI according to this invention.

The image analyzing unit 13, when generating this parametric image Pa, can use the ROI Q0 stored in the storage unit 20. That is, the image analyzing unit 13 generates the parametric image Pa by analyzing the standardized PET images E which have been standardized using the ROI Q0. The standardized PET images E are acquired plurally, and are dynamic images. FIG. 8 schematically shows the ROI Q0 the image analyzing unit 13 refers to at the time of operation. This ROI Q0 is a specific site in the standard brain. The image analyzing unit 13 recognizes a corresponding site on the distribution form display image D1 which is in the same position as the ROI Q0 of the standard data S showing the standard brain, and sets the corresponding site as reference. And the image analyzing unit 13 generates the parametric image Pa by analyzing the dynamic standardized PET images E on a pixel-by-pixel basis based on the reference. This operation will be called normalization hereinafter. That is, the image analyzing unit 13 normalizes its analysis results based on analysis results of the corresponding site on the standardized distribution images. In a diagnosis of Alzheimer's disease, the ROI Q0 is selected to be a site corresponding to the cerebellar cortex of the standard brain. The image analyzing unit 13 corresponds to the normalizing device in this invention.

Thus, the image analyzing unit 13 can carry out an analysis of time variations of the radioactive drug distribution about the corresponding site on the dynamic standardized PET images E which corresponds to the ROI Q0 on the standard data S.

<Operation of the Quantitative Analyzing Unit>

The parametric image Pa is sent to the quantitative analyzing unit 14 which conducts a quantitative analysis of the image. A specific operation carried out by the quantitative analyzing unit 14 will be described. The quantitative analyzing unit 14 acquires the parametric image Pa after normalization from the image analyzing unit 13. And the quantitative analyzing unit 14 automatically reads, by a series of manipulations, data representing the ROI R0 from the storage unit 20.

Figure 9:
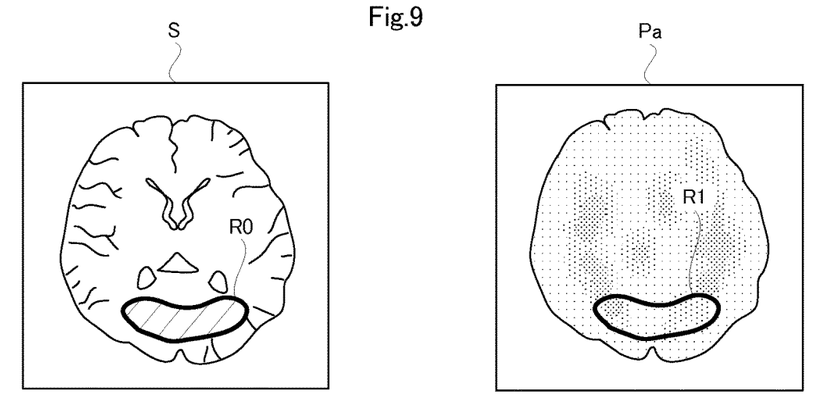
FIG. 9 is a schematic view illustrating the ROI and a corresponding site according to this invention.

The left portion of FIG. 9 schematically shows the ROI R0 which is referred to by the quantitative analyzing unit 14 at the time of operation. This ROI R0 is a specific site in the standard brain. The quantitative analyzing unit 14 recognizes a corresponding site R1 on the parametric image Pa which is in the same position as the ROI R0 of the standard data S showing the standard brain (see the right portion of FIG. 9), and acquires a representative value in the corresponding site R1. Here, the representative value in the corresponding site R1 is a value representing the inside of the corresponding site R1, which may, for example, be an average value of pixel values in the corresponding site R1 or a maximum value of the pixel values in the corresponding site R1. The quantitative analyzing unit 14 quantifies the representative value in the corresponding site R1 based on acquired pixel values. Based on this numerical value, whether the distribution situation of the radioactive drug reflected in the PET images D is abnormal or not. Although a mode of acquiring the representative value in the corresponding site R1 from the parametric image Pa has been described here, a representative value of radioactive concentration in the corresponding site R1 may be acquired based on a radioactive concentration for every pixel on the standardized PET images E, and check an inclination value using that value to acquire a representative value in the corresponding site R1.

The ROI R0 at this time is not particularly limited. For example, the ROI R0 may be set as a site of the hippocampus in the standard brain.

Thus, the quantitative analyzing unit 14 caries out a quantitative analysis on the corresponding site R1 on the parametric image Pa corresponding to the ROI R0 on the standard data S. This operation also means carrying out an analysis of time variations of the radioactive drug distribution about the corresponding site on the standardized PET images E.

<Operation of the Comparing Unit>

The parametric image Pa after normalization is sent to the comparing unit 15. The comparing unit 15 reads a parametric image Pa relating to past analysis results stored in the storage unit 20, and automatically compares the two images through a series of manipulations such as by acquiring differences therebetween. If such comparison is carried out in connection with the same subject, it will be possible to grasp the progression of a lesion in the brain of the subject. If such comparison is carried out in connection with different subjects, the comparison between the subjects will become easy.

The comparing unit 15 may operate using the patterns P stored in the storage unit 20. That is, the comparing unit 15 reads from the storage unit 20 the pattern P which is an analysis result of a normal brain, and the pattern P which is an analysis result of an abnormal brain, and calculates a correlation with the parametric image Pa about a certain specific area. Each pattern P, which is in form of a parametric image, can easily be compared with the parametric image Pa. When the comparing unit 15 determines that the parametric image Pa has a correlation with the pattern P of the abnormal brain rather than the pattern P of the normal brain, the brain of the subject can be diagnosed as having an abnormality. As a specific operation, the comparing unit 15 acquires representative values in the ROI R0 of the respective patterns P, and compares results thereof. In this way, checking is made whether the brain reflected in the parametric image Pa is normal or not.

Alternatively, the comparing unit 15 may analyze the parametric image Pa acquired this time, using other parametric images.

<Operation of the ROI Individualizing Unit>

The ROI individualizing unit 16 is provided for the purpose of transforming the sites of interest Q0, R0 according to the form of the brain measured with the PET apparatus, thereby to estimate the shapes of the sites of interest in the brain measured. The ROI individualizing unit 16 has a function to individualize the shapes of the standardized sites of interest by applying it to the brain measured.

Figure 10:
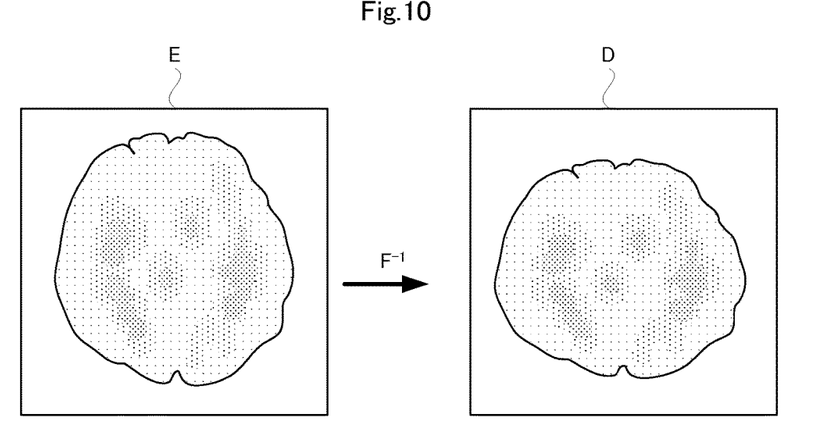
FIG. 10 is a schematic view illustrating operation of a ROI individualizing unit according to this invention.

The ROI individualizing unit 16 acquires the transform function F from the transform function acquiring unit 11. And the ROI individualizing unit 16 calculates an inverse transform function $F^{-1}$ which is the inverse function of the transform function F. This inverse transform function $F^{-1}$ is a function which outputs PET images D when applied to the standardized PET images E as shown in FIG. 10, for example.

Figure 11:
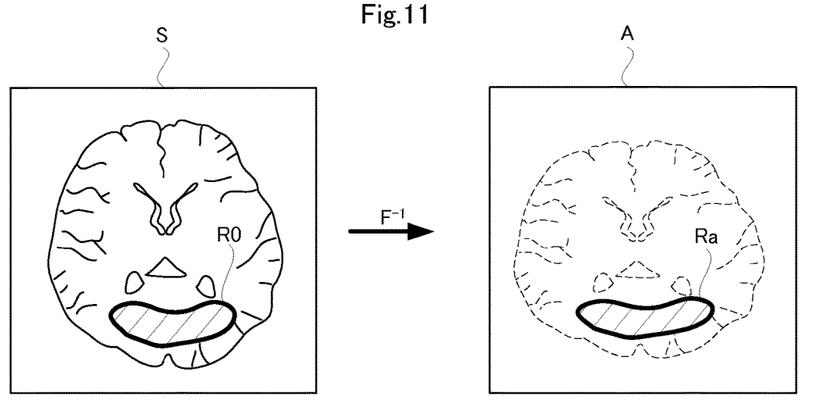
FIG. 11 is a schematic view illustrating operation of the ROI individualizing unit according to this invention.

The ROI individualizing unit 16 acquires the data showing the sites of interest Q0, R0 from the storage unit 20, and applies the inverse transform function $F^{-1}$ to this data. Then, as shown in FIG. 11, the ROI R0 representing part of the standard brain is transformed into an area Ra in the brain measured with the PET apparatus. Supposing the ROI R0 shows the hippocampus, the area Ra represents the position, range and size of the actual hippocampus within the brain measured with the PET apparatus. Thus, the ROI individualizing unit 16 enables guessing the actual shape of a structure within the brain.

Thus, the ROI individualizing unit 16 acquires the ROI on the PET images D by transforming the sites of interest Q0, R0 on the standard data S in a transformation mode which changes the shape of the brain represented by the standard data S into the shape of the brain of the subject appearing in the PET images D.

As described above, the tomographic image analyzing apparatus 1 according to this invention includes the image standardizing unit 12 which transforms PET images D, in advance of a tomographic image analysis, so that the form of the brain of the inspection object appearing in the PET images D become the form of the brain represented by standard data S. According to this invention, therefore, it is not necessary to acquire static PET images or form images for finding out a brain form about the brain of the inspection object appearing in the PET images D. Consequently, compared with conventional techniques, this invention can ease the burden on the subject. Further, with the image analyzing unit 13 provided for applying a ROI obtained from the standard brain to dynamic standardized PET images E, the time of analysis is shortened since it is not necessary to carry out varied image processes which refer to the form images or the like.

According to this invention, the following analysis is conducted concerning the standardized PET images E generated after transformation. That is, an analysis of time variations of radioactive drug distribution in the corresponding site R1 on the standardized PET images E which corresponds to the ROI R0 on the standard data S is automatically conducted in a series of operations. Such measure assures highly accurate and stable analysis results. According to a conventional technique, a site of interest is manually set to PET images D. With such construction, a range division of a structure within the brain cannot be carried out stably, and an analysis of dynamic PET images is impossible. This invention, however, can automatically carry out this setting of a ROI, can automatically acquire time variations within the ROI in the dynamic PET images with lapse of time, and can obtain a parametric image by direct image analysis of the time variation data, thereby eliminating room for subjectivity entering the analysis to render results of the analysis stable and highly precise.

According to the above construction, the ROI individualizing unit 16 is provided for acquiring the ROI on the PET images D by transforming the ROI on the standard data S. Such construction enables the shapes of sites of interest different between the brains of subjects to be grasped simply and conveniently.

This invention is not limited to the construction described above, but may be modified as follows:

(1) In the foregoing description, the transform function F is a function for transforming two-dimensional images longitudinally and transversely. In this invention, instead of the above arrangement, the transform function F may be a function for transforming three-dimensional voxel data longitudinally, transversely and vertically. In the foregoing description, the PET images D are images on a certain plane, but in fact, in imaging with a PET apparatus, a plurality of PET images D are acquired from different slice planes parallel to one another in one imaging. It is therefore possible to acquire voxel data in a three-dimensional arrangement of the radioactive drug by arranging each of the PET images D on a corresponding slice plane. Considering that the PET images D are imaged repeatedly at different points of time, a plurality of boxel data in a three-dimensional arrangement of the radioactive drug can be acquired at the different points of time by imaging using the PET apparatus.

Operation of the transform function acquiring unit 11 in such modification will be described. The transform function acquiring unit 11 selects and totals appropriate ones of the plurality of voxel data of different imaging points of time, to acquire a three-dimensional shape of the brain measured with the PET apparatus. What serves as an index when the transform function acquiring unit 11 selects voxel data is a time taken from injection of the radioactive drug to imaging. It is known that, after injection of the radioactive drug, the radioactive drug will pervade the entire brain in a certain period of time. The transform function acquiring unit 11 generates the three-dimensional shape by totaling the voxel data imaged before or after this period of time. The transform function acquiring unit 11, by comparing the three-dimensional form of the brain of the subject represented by the voxel data and the three-dimensional form of the brain shown by the standard data S, acquires a transform function F for transforming the three-dimensional form of the brain of the subject represented by the voxel data into the three-dimensional form of the brain in the standard data S.

(2) The tomographic image analyzing apparatus 1 according to this invention has been described as analyzing images acquired by a PET apparatus. However, this invention is not limited to this, but may also be applicable to an analysis of images obtained by a SPECT apparatus.

INDUSTRIAL UTILITY

As described above, this invention is suitable for the medical field.

REFERENCE SIGNS LIST

D PET images (dynamic distribution images)
E standardized distribution images
P patterns
Q0 ROI
R0 ROI
R1 corresponding site
S standard data
11 transform function acquiring unit (transform function acquiring device)
12 image standardizing unit (distribution image standardizing device)
13 image analyzing unit (analyzing device, normalizing device)
14 quantitative analyzing unit (analyzing device)
15 comparing unit (comparing device)
ROI individualizing unit (ROI individualizing device)
20 storage unit (storage device)

The invention claimed is:

1. A tomographic image analyzing apparatus for analyzing dynamic distribution images, which are tomographic images, acquired at a slice plane of a brain at different times over a predetermined period of time to show a distribution of a radioactive drug through the brain, the apparatus comprising:
    a storage device storing beforehand standard data showing a shape of a standard brain;
    a distribution image standardizing device transforming a form of the brain in the dynamic distribution images into a form of the standard brain shown in the standard data by selecting one image in which the form of the brain is recognizable from the dynamic distribution images and by comparing the form of the brain in the one image and the form of the standard brain, whereby the dynamic distribution images are converted to standardized distribution images showing the distribution of the radioactive drug; and
    an analyzing device carrying out an analysis of time variations of radioactive drug distribution based on the standardized distribution images.

2. The tomographic image analyzing apparatus according to claim 1, further comprising a transform function acquiring device acquiring, based on the comparison, a transform function for use by the distribution image standardizing device.

3. The tomographic image analyzing apparatus according to claim 1, comprising:
    a storage device storing beforehand a region of interest on the standard data,
    wherein the analyzing device carries out an analysis of time variations of the radioactive drug distribution about a site that corresponds to the region of interest on the standard data.

4. The tomographic image analyzing apparatus according to claim 3, comprising a normalizing device normalizing analysis results of the analyzing device based on analysis results in the corresponding site on the standardized distribution images.

5. The tomographic image analyzing apparatus according to claim 1, wherein:
    the storage device stores a pattern of the time variations of the radioactive drug; and
    a comparing device is provided for comparing the analysis results of the analyzing device and the pattern.

6. The tomographic image analyzing apparatus according to claim 5, wherein:

the storage device stores analysis results of a normal brain outputted by the analysis device; and the comparing device compares the analysis results of the analyzing device and the analysis results of the normal brain.

7. The tomographic image analyzing apparatus according to claim 5, wherein:

the storage device stores past analysis results outputted by the analyzing device; and the comparing device compares the analysis results of the analyzing device and the past analysis results.

8. The tomographic image analyzing apparatus according to claim 1, comprising a region of interest individualizing device transforming a site of interest on the standard data by changing the shape of the brain shown in the standard data into the shape of the brain in the dynamic distribution images.

* * * * *